United States Patent [19]
Santana et al.

[11] Patent Number: 5,830,211
[45] Date of Patent: Nov. 3, 1998

[54] PROBE TO TREAT VIRAL LESIONS

[76] Inventors: Jose A. Santana; Janet K. Santana, both of 283 Savona St., Goleta, Calif. 93117; Michael D. Rudnick, 2820 S. Harlan Way, Denver, Colo. 80227

[21] Appl. No.: 814,503

[22] Filed: Mar. 10, 1997

[51] Int. Cl.⁶ ................................... A61B 17/38
[52] U.S. Cl. ............................... 606/27; 607/88
[58] Field of Search ............... 606/1, 2, 10–12, 606/27–31; 607/88, 96; 600/108

[56] References Cited

U.S. PATENT DOCUMENTS

| | | |
|---|---|---|
| 4,090,517 | 5/1978 | Nagatoki . |
| 5,009,655 | 4/1991 | Daignault et al. ........................ 606/7 |
| 5,376,087 | 12/1994 | Haber et al. ............................. 606/27 |
| 5,500,009 | 3/1996 | Mendes et al. . |

*Primary Examiner*—Michael Peffley
*Assistant Examiner*—Roy Gibson
*Attorney, Agent, or Firm*—James E. Brunton

[57] ABSTRACT

A method and apparatus for treating lesions caused by viral infections including herpes simplex. The apparatus comprises a compact, easy-to-use instrument for controllably providing heat to the lesion site both from a primary built-in heat source and from a built-in light source which functions to complement the primary heat source and also to brightly illuminate the lesion site. The instrument also includes a novel bar graph, multicolor display which provides a visual indication of the instrument power setting as well as temperature conditions at the lesion site. Additionally, the instrument provides an audio signal to the user when the proper length of treatment time has elapsed.

15 Claims, 3 Drawing Sheets

U.S. Patent  Nov. 3, 1998  Sheet 1 of 3  5,830,211
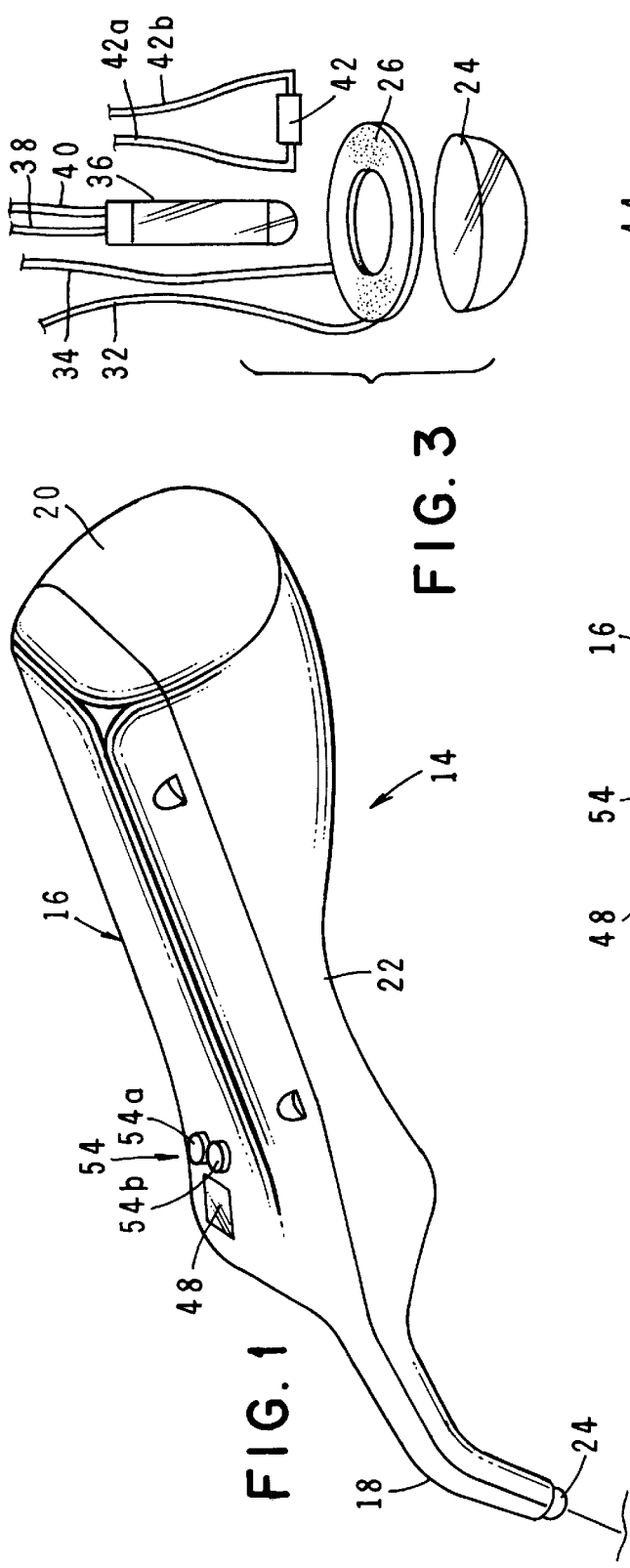
FIG. 1
FIG. 3
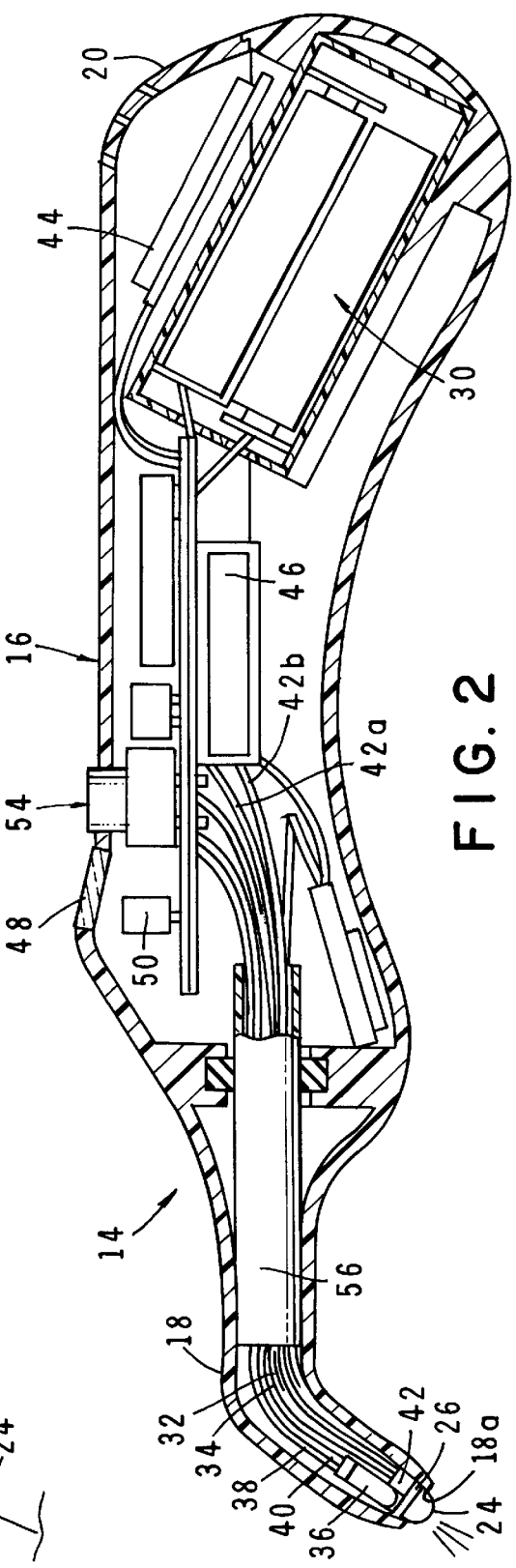
FIG. 2

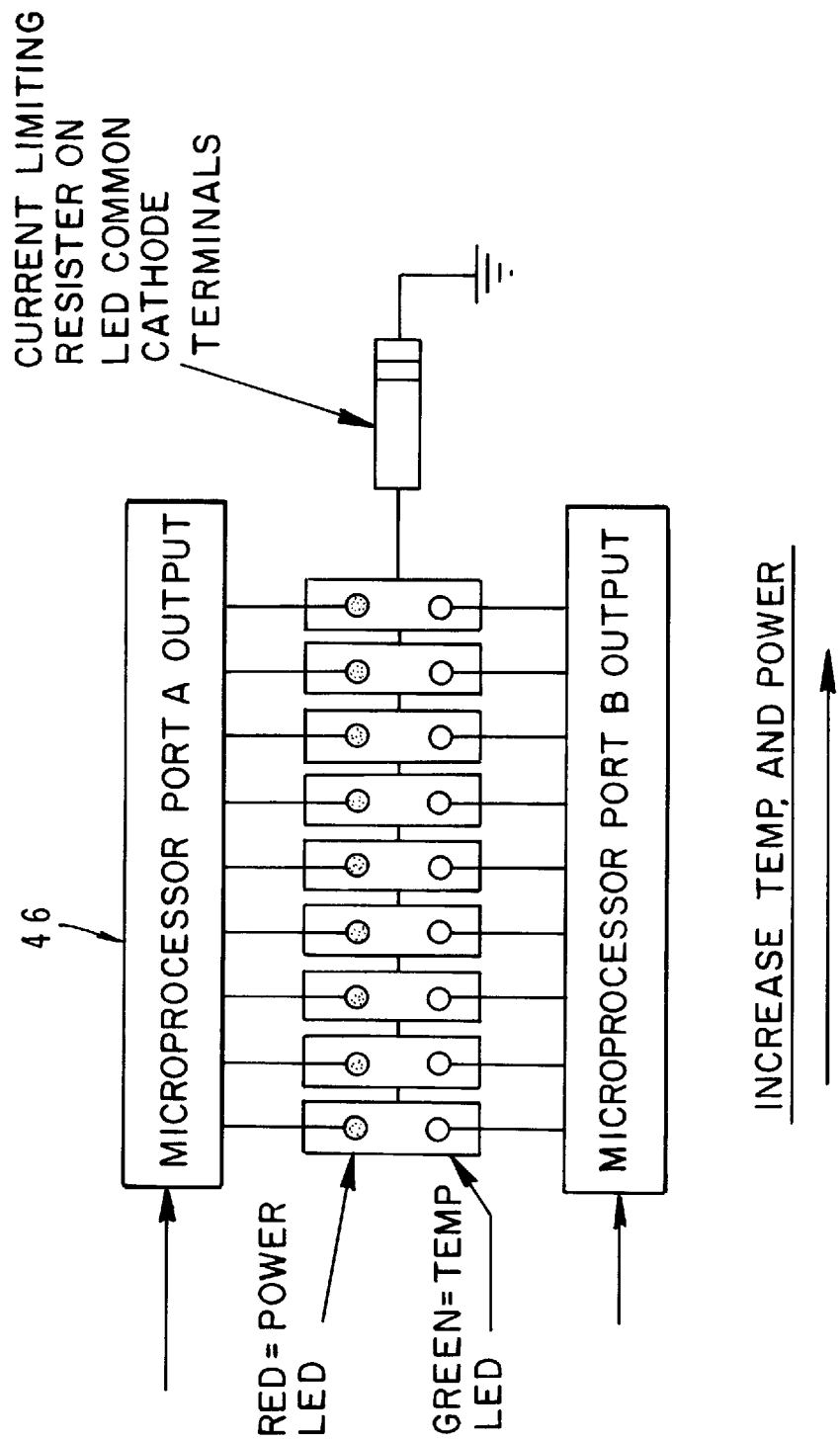

PROBE TO TREAT VIRAL LESIONS

BACKGROUND OF THE INVENTION

1. Field of the Invention

The present invention relates generally to medical appliances. More particularly, the invention concerns an appliance for treating viral lesions such as herpes simplex lesions.

2. Description of the Prior Art

Viral infections in humans are quite common. One such infection which is particularly painful and troublesome is the herpes infection. This infection is typically characterized by clusters of vesicles on the skin or mucous membranes such as the lips, mouth or vulva. Herpes infections and particularly herpes simplex infections can be extremely painful and strike males and females of all ages and races.

A number of treatments for viral infections have been suggested in the past. Such treatments include topical medicinal treatment, laser therapy and thermal stimulus. Topical treatments, while sometimes providing temporary relief, have been shown to be generally ineffective. On the other hand, laser light therapy using minimum powered infrared lasers has shown some promise. Similarly, methods for relieving herpes pain by illumination using a light emitting diode (LED) have been somewhat effective in selected cases. Such methods are disclosed in U.S. Pat. No. 5,500,009 issued to Mendes et al. The methods described in this latter patent involve providing a plurality of light emitting diodes which generate non-coherent radiation in a narrow band width, driving the diodes to generate non-coherent radiation in a continuous wave mode, with concentration of the radiation on the surface area afflicted with herpes or other agent.

One type of medical appliance for practicing moxibution at locations within the human body, such as within the mouth, is described in U.S. Pat. No. 4,090,517 issued to Nagatoki. The Nagatoki device comprises a hand-held housing enclosing an electrical heater and a control therefor. A number of presser elements can be interchangeably secured to one end of the device and extend therefrom. The presser elements are in contact with a plate-like element heated by the heater. In use the heated presser element is pressed against the affected area to cause heat stimulation and to create an acupuncture-like effect.

The thrust of the present invention is to provide a novel, easy-to-use instrument which is superior to the prior art devices and remedies and effectively eliminates the pain and discomfort resulting from certain infections, including herpes simplex.

SUMMARY OF THE INVENTION

It is an object of the present invention to provide a novel method and apparatus for treating viral infections including herpes simplex.

More particularly, it is an object of the invention to provide a compact, easy-to-use instrument for controllably providing heat to the lesion site both from a primary built-in heat source and from a built-in light source which functions to compliment the primary heat source and also to brightly illuminate the lesion site.

In this regard, and by way of background, a variety of alternative heating methods used to generate the required temperature range were considered. These included the use of non-thick film heater elements, such as Nichrome wire heater elements, solid state devices such as transistors operating in a thermal dissipative mode. In addition, a temperature-controlled, externally pumped, circulating fluid device that delivers heat to the lesion site was considered. The device made use of a peristaltic pump which circulated a liquid contained within the tubing. The tubing itself was immersed in a temperature controlled bath, enabling it to absorb heat from the surrounding liquid media. Other methods considered involved the use of substances which could store heat, such as those found in chemical salts contained in flexible plastic pouches. Such devices are readily commerically available and are used to apply heat to injuries after being heated in a microwave oven, or the like, for some period of time. However, temperature control using the fluid system, was found to be difficult to control. Due to the system's slow temperature response time, the heated salts had no way to increase their temperature to compensate for variations in the heat load.

Thermoelectron Peltier Pumps were considered, but not tried due to excessive current consumption preventing the reasonable use of batteries as the power source.

Experiments showed that the Nichrome wire heater system could actually benefit from the temperature coefficient of resistance property of the wire. It was found that this change in resistivity of the heater element could in itself be used to control and maintain constant power through the heater element during varying loads. Finally, a more responsive in-situ heating and temperature sensing method as further described herein was opted as a preferred operational system.

Another object of the invention is to provide an instrument of the character described which includes a novel bar graph, multicolor display which provides a visual indication of the instrument power setting as well as temperature conditions at the lesion site.

Another object of the invention is to provide an instrument as described in the preceding paragraph which also provides an audio signal to the user when the proper length of treatment time has elapsed.

BRIEF DESCRIPTION OF THE DRAWINGS

FIG. 1 is a generally perspective view of one form of the apparatus of the invention.

FIG. 2 is an enlarged, side-elevational, cross-sectional view of the apparatus shown in FIG. 1.

FIG. 3 is a fragmentary, exploded view of the tip assembly of the apparatus shown in FIG. 1.

FIG. 5 is a generally diagrammatic view of the power temperature LED display of one form of the invention.

DESCRIPTION OF THE INVENTION

Figure 4:
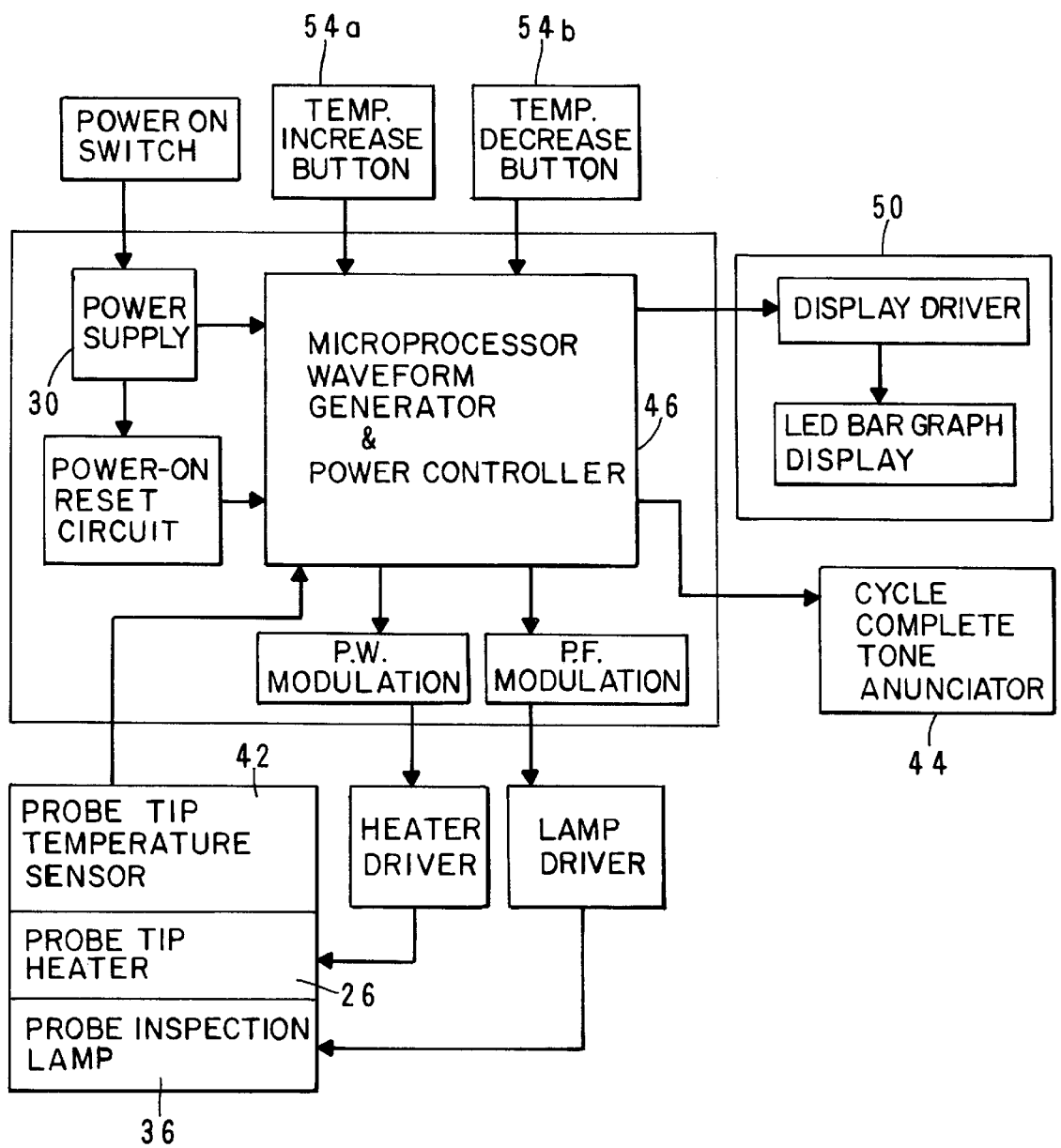
FIG. 4 is a generally diagrammatic, block diagram type view showing the interrelationship of the various components of the apparatus of one form of the invention.

Referring to the drawings and particularly to FIGS. 1, 2, and 3, one form of the appliance of the invention for treating lesions is there illustrated and generally identified by the numeral 14. The appliance here comprises a hollow housing 16 having a first end portion 18, a second end portion 20 and an intermediate, hand-grip portion 22. Disposed within the forward first end portion of housing 18 are heating means for providing a heat source and light means for generating a light beam and directing it toward an opening 18a formed in the first end portion of the hollow housing. Disposed within opening 18 is a lens means for diffusing the light beam generated by the light means and for conducting heat generated by the heat source. As shown in FIG. 2, the lens means, which is here provided in the form of a generally dome-shaped, cast silicone lens 24, closes opening 18a formed in first end portion 18 of housing 16.

As best seen by referring to FIG. 3, the heating means of the present form of the invention comprises a plurality of thick film resistors 26 connected in series and powered by power means, shown here as a battery power pack 30 which is housed within second end portion 20 of hollow housing 16. Battery power pack 30 is of a type well known to those skilled in the art and is readily commercially available. Electrical conductors 32 and 34 conduct electricity from battery power pack 30 to thick film resistors 26 via control means, the character of which will be described presently.

The light means of the form of the invention shown in the drawings comprises a miniature halogen light bulb 36 which is also driven by power pack 30 via electrical connectors 38 and 40. As also shown in FIG. 3, forming a part of the control means of the invention for controlling the heating means is sensor means, here provided in the form of a silicon diode probe tip temperature sensor 42, which is operably interconnected with the heating means or substrate 26 (see also FIG. 4).

Also forming a part of the control means of the present invention is audio means for generating an audio signal under certain operation conditions. As best seen in FIG. 2, this, audio means here takes the form of a piezo electric speaker 44 which is also of a character well known to those skilled in the art and is readily commercially available from various commercial sources. In addition to the audio means, the control means of the invention further includes a microprocessor 46 which is disposed within hollow housing 16 and is operably interconnected with and strategically controls the heating means, the light means, and the audio means of the invention. As indicated in FIGS. 2 and 4, also interconnected with microprocessor 46 is the important display means of the invention for displaying temperature conditions that exist at any point in time at a location proximate first end portion 18 of the apparatus. As best shown in FIG. 2, the display means of the invention for displaying temperature conditions proximate the lens area of the apparatus includes a light emitting diode display window 48 and a light emitting power/temperature graph display 50.

Referring particularly to FIG. 2, it is to be noted that electrical conductors 38 and 40 interconnect halogen light bulb 36 with a temperature control button assembly 54. Similarly, electrical connector 32 of the heating means is interconnected with temperature control button assembly 54. Electrical connectors 42a and 42b interconnect the sensor means of the invention, which is shown here as silicon diode temperature sensor 42, with the microprocessor 46. Temperature sensor 42 is also of a character well known to those skilled in the art and is readily commercially available. As indicated in FIG. 2, the various electrical connectors leading to the heating means, lighting means and sensor means are safely enclosed within a rubber grommet 56 which is disposed within a neck-down portion 18a of first end portion 18 of housing 16.

Referring particularly to FIGS. 4 and 5, the operation of the appliance of the present invention will now be described. As a first step, energization of the apparatus is accomplished by depressing either one of the two push buttons 54a or 54b which buttons comprise the temperature control assembly 54 of the invention (see FIG. 1). This step signals an interrupt to the microprocessor which would previously have gone into a dormant, or sleep mode stage, after either manually turning off the apparatus or after a period of inactivity of the apparatus for approximately 15 minutes. In the event of either a power-on detection signal or the interrupt signal, the microprocessor proceeds to a predetermined memory location known as the "interrupt vector" where it calls up the address of the power-up routine. This done, the Assembly Language Code is executed which causes the apparatus to properly function. The development of the power-up routine and assembly language code is well within the skill of the art and can be readily programmed into the microprocessor by a competent programmer.

The initial step required by the Assembly Language Code is to turn off all output devices. This, of course, prevents any mistakes from occurring. The second event to occur is to sense the probe tip temperature by digitizing the voltage produced by the probe tip temperature sensor 42. This comparison will enable the microprocessor to activate the correct light emitting diodes on the display 50. In the present instance, this display is made up of two color light emitting diodes for each of the eight positions on the linear array of diodes (see FIG. 5). By convention, temperature information is shown as a green bar of light forming a scale which increases in temperature to the right of the display. On the same axis, the LED display also conveys power setting to the heater 26 disposed in first end 18 of the housing. This information is displayed as a red light bar which increases in power to the right of the display. The actual power setting is only assigned to one particular LED at a time. When the power LED position is identical to the position of the temperature scale, that is when the two coincide in place, the microprocessor turns on both LEDs to change the color to yellow. In this manner, it is possible to convey three degrees of freedom (three variables) with one display. The color combinations are determined by the microprocessor from the contents of a search and look-up table, the character and development of which is well understood by those skilled in the art.

The next item considered by the microprocessor is to sense the presence of a "power demand" as, for example, a temperature increase call. The microprocessor scans on a regular basis the push buttons 54a and 54b on the control panel. It is here that the microprocessor determines how much power to apply to the heating means or heater 26 by noting how long or how often the power demand button is depressed. Every time the microprocessor senses a demand for power, it advances the appropriate LED (that, is to the right of the display) and changes the duty cycle of a pulse width modulated square wave on one of its output pins. This signal is used to directly control the gate of the "Mosfet" power transistor 60 which is housed within hollow housing 16 in the manner shown in FIG. 2. Mosfet power transistor 60, which is readily commercially available, functions to control the turn-on or turn-off duty cycle of the resistive heater 26. Power is controlled by alternatively changing the ratio of the signals on time to that of the signals off time (hence the classical pulse width modulation) or P.W.M. OUTPUT.

During the time at which the microprocessor sends a P.W.M. signal to the heater power "Mosfet" drive transistor 60, it also sends a frequency modulated (F.M.) signal or P.F.M. pulse frequency modulated signal to a second power transistor which controls the light means or halogen light bulb 36. The light generated by the light means is primarily used as illumination during the lesion inspection phase of the treatment. However, during probe operation, the light bulb starts to blink faster as the power is increased. The purpose of this action is to enable the end user to determine on-sight a relative power setting of the probe even when the control panel cannot be readily observed as, for example, when within the mouth of the patient. This manner of operation permits the "blind" setting and visual verification of any power change. This step is accomplished by the user looking into a mirror and viewing the lesion sore while holding the tip of the appliance to the herpes lesion. In this regard, it is important to maintain constant visual feedback of any power changes, since within a short period after the power setting change is made, the temperature of the heater could increase considerably causing the user to detect a significant, perhaps uncomfortable, change.

Another task which is uniquely accomplished by the microprocessor of the appliance is to maintain a constant duty cycle satisfying the required temperature demanded by the push of the control button(s). This routine examines the voltage delivered by the temperature sensor 42 and functions to control the temperature of the heater element 26 by a plus or minus 5% automatic variation of the setting. This is done to accommodate continually varying temperature feedback signals based on changes in tissue density and thermal dissipation into the tissue which surrounds the lesion site. This unique feature frees the user from having to continually change settings if the appliance is being used to cover a broad area.

While the cycle or treatment is in progress, the microprocessor also keeps track of the time (in seconds) during which the tip of the appliance has remained within a predetermined temperature error band. When the time requirement is completed, the important audio means notifies the user by beeping a 500 hertz tone. At the discretion of the user, the treatment can either be immediately terminated or continued depending on the circumstances at hand. Preferably the audio signal occurs only once during each complete cycle. As previously mentioned, at the end of a set time period, such as 15 minutes, the appliance will automatically go into a stand-by mode and will automatically power down.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An appliance for treating lesions comprising:
   (a) a hollow housing having a first end portion having an opening therein, a second open end portion and an intermediate hand grip portion;
   (b) heating means disposed within said hollow housing for providing a heat source;
   (c) light means disposed within said hollow housing for generating a light beam and directing it toward said opening in said first end portion of said housing;
   (d) lens means for diffusing said light beam and for conducting heat generated by said heat source, said lens means being connected to said first end portion of said hollow housing to close said opening therein; and
   (e) control mean disposed within said hollow housing for controlling said heating means and said light means.

2. An appliance as defined in claim 1 in which said lens means comprises a cast silicone lens.

3. An apparatus as defined in claim 1 further including display means for displaying temperature conditions proximate said first end portion of said housing.

4. An apparatus as defined in claim 1 in which said control means includes audio means for generating an audio signal.

5. An apparatus as defined in claim 4 in which said audio means comprises a piezoelectric speaker disposed within said hollow housing.

6. An apparatus as defined in claim 5 in which said control means further includes a microprocessor disposed within said hollow housing and operably interconnected with said heating means, said light means, said display means and said audio means.

7. An appliance for treating lesions comprising:
   (a) a hollow housing having a first end portion, a second end portion and an intermediate hand grip portion, said first end portion including an outwardly extending hollow tip having an opening;
   (b) a heating element disposed within said hollow tip proximate said opening for generating heat within said hollow tip;
   (c) light means disposed within said hollow housing for generating a light beam and directing it toward said second opening in said hollow tip;
   (d) a generally hemispherically shaped lens constructed and arranged to close said opening in said hollow tip, said lens functioning to diffuse said light beam and to conduct and diffuse heat generated by said heating element;
   (e) control means disposed within said hollow housing for controlling said heating element and said light means; said control means including:
      (i) a sensor disposed within said hollow tip for sensing heat generated by said heating element and for generating a signal corresponding thereto; and
      (ii) a microprocessor disposed within said hollow housing and operably interconnected with said sensor for receiving signals generated thereby;
   (f) display means connected to said microprocessor for displaying temperature conditions at a location proximate said lens.

8. An apparatus as defined in claim 7 in which said control means further includes audio means for generating an audio signal.

9. An apparatus as defined in claim 8 in which said audio means comprises a piezoelectric speaker disposed within said hollow housing.

10. An appliance for treating lesions comprising:
   (a) a hollow housing having a first end portion, a second end portion and an intermediate hand grip portion, said first end portion including a outwardly extending hollow tip having an opening;
   (b) a plurality of thick film resistors disposed within said hollow tip proximate said opening for generating heat within said hollow tip;
   (c) light means disposed within said hollow body for generating a light beam and directing it toward said second opening in said hollow tip, said light means comprising a halogen light bulb;
   (d) a generally hemispherically shaped silicone lens constructed and arranged to close said opening in said hollow tip, said lens functioning to diffuse said light beam and to conduct heat generated by said thick film resistors;
   (e) control means disposed within said hollow housing for controlling said thick film resistors and said halogen light bulb, said control means including:
      (i) a silicon diode sensor disposed within said hollow tip for sensing heat generated by said heating element and for generating a signal corresponding thereto; and (ii) a microprocessor disposed within said hollow housing and operably interconnected with said sensor for receiving signals generated thereby;

(iii) audio means connected to said microprocessor for generating an audio signal; and (f) display means connected to said microprocessor for displaying temperature conditions at a location proximate said lens.

11. An apparatus as defined in claim 10 in which said audio means comprises a piezoelectric speaker disposed within said hollow housing.

12. An apparatus as defined in claim 10 in which said display means comprises a plurality of light emitting diodes mounted on said hollow housing.

13. An apparatus as defined in claim 10 further including a power source connected to said thick film resistors and halogen light bulb to cause said halogen light bulb to blink as power is increased from said power source to said plurality of thin film resistors.

14. An apparatus as defined in claim 13 in which said microprocessor automatically interrupts power from said power source after the expiration of a set time period.

15. An apparatus as defined in claim 13 in which said microprocessor keeps track of the time during which the thick film resistors have been energized and at the expiration of a set time period causes said audio means to generate an audio signal.

\* \* \* \* \*